United States Patent [19]
Smith et al.

[11] Patent Number: 6,110,505
[45] Date of Patent: Aug. 29, 2000

[54] TRANSLUCENT ANTACID SUSPENSION CONTAINING CO-DRIED DIHYDROXY ALUMINUM SODIUM CARBONATE

[75] Inventors: Bruce P. Smith, Blue Bell; John J. Dubek, Philadelphia; Gerard P. McNally, Strafford, all of Pa.

[73] Assignee: McNeil PPC Inc., New Brunswick, N.J.

[21] Appl. No.: 08/829,979

[22] Filed: Apr. 1, 1997

[51] Int. Cl.[7] .............................. A61K 9/10; A61K 33/10
[52] U.S. Cl. ......................... 424/686; 424/455; 424/489; 514/819; 514/937
[58] Field of Search ................................. 424/489, 466, 424/455, 686; 514/819, 937

[56] References Cited

U.S. PATENT DOCUMENTS

| | | | |
|---|---|---|---|
| 4,112,072 | 9/1978 | Rubino et al. | 424/155 |
| 4,115,553 | 9/1978 | Rubino et al. | 424/155 |
| 4,438,085 | 3/1984 | Kaufman | 423/419 P |

OTHER PUBLICATIONS

A. DeVos, et al., Journal of Pharmaceutical Sciences; V83, pp. 641–643, 1994, "Release of Indomethacin From Transparent Oil–Water Gels", Abstract 14/7/1.

D.D. Jordan, Journal of Pharmaceutical Sciences, V82, pp. 1269–1271, 1993, "Optical Crystallographic Characteristics of Some USP Drugs", Abstract 14/7/2.

S. Tichy, Seifen, Oele, Fette, Wachse (Germany) V119, (Jun. 8) pp. 482, 484–490, 1993, "Transparent ZNO For Skin and Sun Protection", Abstract 14/7/3.

J. Moller–Kemsa, Parfuemerie und Kosmetik (Germany) V74, (May), pp. 323–326, 1993, "Color Measurement of Transparent Fluids", Abstract 14/7/4.

A. Devos et al., International Journal of Pharmaceutics (Netherlands), V92, (May 3, 1993) pp. 191–196, "Solubilization and Stability of Indomethacin in a Transparent Oil–Water Gel", Abstract 14/7/5.

V. Peikov et al., Journal of Dispersion Sciences and Technology (USA), v14, (4), pp. 499–512, 1993 "Electro–Optical Determination of Alpha–FEOOH Particle Sizes", Abstract 14/7/6.

J. Mattai et al., Journal of the Society of Cosmetic Chemists (England), V44, (Mar.–Apr.)., pp. 89–100, 1993, "Prevention of Model Stratum Corneum Lipid Phase Trnasitions In Vitro by Cosmetic Additives—Differential Scanning Calorimetry, Optical Microscopy", Abstract 14/7/7.

R. Evans, Pharmaceutical Technology (USA) v17, (Mar), pp. 146–148, 150, 152, 1993, "Determination of Drug Particle Size and Morphology Using Optical Microscopy", Abstract 14/7/8.

F. Comelles, et al., International Journal of Cosmetic Science (England), V14, (4), pp. 183–195, 1992, "Transparent Gels: Study of Their Formation and Assimilation Of Active Ingredients Through Phase Diagrams", Abstract 14/7/9.

S. Tichy, Seifen, Oele, Fette, Wachse (Germany) V118, (Jun. 30), pp. 612, 614–616; 618–620, 1992, "Transparent TIO2 For UV–Protection", Abstract 14/7/10.

B. Goldlman, Pharmaceutical Engineering (USA), V12, (Jan.–Feb., pp. 14, 16–17, 1992, Optical Disk Technologies Clear Paper Bottlenecks At Upjohn, Abstract 14/7/11.

A. Thurn–Muller et al., Seifen, Oele, Fette, Wachse (Germany) V117 (Dec. 12), pp. 775–776, 1991 "Transparent Colors", Abstract 14/7/12.

(List continued on next page.)

*Primary Examiner*—Thurman K. Page
*Assistant Examiner*—James M. Spear
*Attorney, Agent, or Firm*—Connolly and Hutz

[57] ABSTRACT

The invention provides an essentially translucent liquid antacid composition with dihydroxyaluminum sodium carbonate (DASC) as the active ingredient. The DASC is prepared by co-drying DASC with a polyol, and the resulting co-dried DASC/polyol is mixed with water to form the liquid composition. The antacid composition preferably contains additional polyol to further improve the translucency of the liquid composition.

13 Claims, 3 Drawing Sheets

OTHER PUBLICATIONS

G. Whalley, Manufacturing Chemist (England) V62, (Oct.), p. 47, 49, 1991, "Updating Transparent Soap Manufacture", Abstract 14/7/13.

F. Comelles, International Journal of Cosmetic Science (England), V12, (5), pp. 185–196, "Transparent Formulations of a Liposoluble Sunscreen Agent In an Aqueous Medium", Abstract 14/7/14 1995.

J. Blattner, Pharmazeutische Industrie (Germany) V53, (4), pp. 397–400, 1991, Verification and Inspection of Safety Workbenches and Laminar Flow Boxes, "Particle Generators, Dilution System and Optical Particles Counters as Major Components of Coincidence Error–Free and Reproducible Verification Methods and Tests", Abstract 14/7/15.

C. Provost, et al., International Journal of Pharmaceutics (Netherlands) V62 (Jul. 31), pp. 217–228, 1990, "Transparent Oil–Water Gels. Part 2. Study of the Gel Structure In Transparent Oil–Water Gels By Differential Scanning Calorimetry", Abstract 14/7/16.

R. Caldow, et al., Journal of Parenteral Science and Technology, V43, (Jul.–Aug.), pp. 174–179, 1989, "Procedure To Verify The Lower Counting Limit Of Optical Particle Counters", Abstract 14/7/17.

C. Provost, et al., Drug Development and Industrial Pharmacy (USA), V15, pp. 25–49, 1989, "In Vitro Penetration of Hydrophilic and Lipophilic Drugs Form Transparent Oil–Water Gels Through Excised Human Epidermis:Comparative Study With Other Dermatological Vehicles", Abstract 14/7/18.

C. Provost et al., Pharmazeutische Industrie (Germany) V50, (1), pp. 1190–1195, 1988, Transparent Oil–Water Gels: Study of Some Physico–Chemical and Biopharmaceutical Characteristics. Part 3. Viscosity and Conductivity, 14/7/19.

H. Beume, Pharmazeutische Zeitung (Germany), V133, (Aug. 25), pp. 19–22, 1988; "Transparency of Drug Quality Necessary For Rational Therapy", Abstract 14/7/20.

E. Nurnberg, Pharmazeutische Industrie (Germany) V48, (12) pp. 1554–1556, 1986, "Transparent Ternary Surfactant Gels. Part 7. Stability Tests", Abstract 14/7/21.

E. Nurnberg, et al., Pharmazeutische Industrie (Germany) V48, (Oct.) pp. 1191–1196, 1986, "Transparent Ternary Surfactent Gels. Part 6. Drugs Containing Surfactant", Abstract 14/7/22.

E. Nurnberg, Pharmazeutische Zeitung (Germany) V131 (Apr. 3), pp. 796–800, 1986, "Polyols As Preservatives for Hydrophilic Creams and Transparent Tenside", Abstract 14/7/23.

N. Anikina et al., Farmatsiya (Moscow, USSR) V35, (4) pp. 78–80, 1986, "Transparency of Packaging Materials: Methods for Assessment and Standards Standards", Abstract 14/7/24.

P. Besancon, et al., S.T.P. Pharma Pratiques (France), V1, (Jun.), pp. 508–515, 1985, "Comparison of Particle Size Distribution Measurements by Sieving and Optical Microscopy—Mesodiameter Statistic", Abstract 14/7/25.

M.D. Rodriguez et al., Ars Pharmaceutica (Spain) V25, (3) pp. 317–330, 1984 "Optical Study of the Shape and Form of the Particles of Talcum Powder", Abstract 14/7/26.

E. Nurnberg, et al., Acta Pharm. Technol., V30, (2), pp. 169–173, 1984 "Mechanics of Oscillation in a Transport Tenside Gel. Part 3. Properties of Three–Component Transparent Tenside Gels", Abstract 14/7/27.

T. Liske et al., Pharmazeutische Industrie (Germany) V46, (3) pp. 291–296, 1984, Trnasparent Foil Self–Adhesives For Ampuls, Abstract 14/7/28.

L. M. Gan, et al., Journal of Dispersion Sciences and Technology (USA), V4, (3), pp. 291–312, "Polymerization in the Transparent Water–In–Oil Solutions. Part 1 Methyl Methacrylate and The Copolymerizable Cosurfactant", Abstract 14/7/29 1983.

Jarson et al., Pharm. Industrie (Germany) vol. 44 (5), 509–515 (1982) Abstract 14/7/30.

A.R. Campanelli et al., Farmaco Ed. Prat., V36, (Jan.) pp. 30–35, 1981, "Optical Study of Tingenone Solubilized in Aqueous Sulution of Sodium Deoxycholate", Abstract 14/7/31.

M. I. Barnett, International Journal of Pharmaceutics (Netherlands), V6 (Aug.) 1980 pp. 131–136, "Importance of Optical Refraction in Connection with the Surface Area Measurement of Powders by Some Photometric Apparatus", Abstract 14/7/32.

W. J. Passl, et al, Physics and Engineering Lab., DSIR, New Zealand Analyst, V105, (May), pp. 512–515, 1980, "Nondestructive Optical Screening Method for Particulate Matter in Intravenous Solutions", Abstract 14/7/33.

D. Schipper et al., J. Parenter. Drug Assoc. V32, (May–Jun.), pp. 118–126, 1978, "Comparison of Optical Electornic Inspection and Manual Visual Inspection", Abstract 14/7/34.

A. Schwab et al., Journal of Dispersion Sciences and Technology (USA), V4, (1), pp. 1–7, 1983 "Triglyceride/Aqueous Ethanol/1–Butanol Microemulsions", Abstract 14/7/35.

S. Srcic et al., Farmacevtski Vestnik (Yugoslavia) V33, (Mar.), pp. 9–14, 1982 Determination of Relative Molecular Masses of Methacrylic Acid and Methylmethacrylate Copolymers (Eudispert). Abstract 20/7/11.

R.C. Rowe, Journal of Pharmacy and Pharmacology (England), V35, (Jan.) pp. 43–44, 1983 "Orientation and Alignment of Particles in Tablet Film Coatings", Abstract 20/7/12.

R. C. Rowe, Journal of Pharmacy and Pharmacology (England) V35, (Apr.) pp. 205–207, 1983, "Refractive Indices Of Polymer Film Formers, Pigments and Additives Used In Tablet Film Coating: Their Significance and Practical Application", Abstract 20/7/13.

H. Kassebaum, Krankenhauspharmazie (Germany), V3, (May–Jun.), pp. 80–82, 1982, "Inprocess Control of Large Volume Parenteral solutions With Physical Measuring Data", Abstract 20/7/14.

Yalabik–Kas, H.S. et al., Drug Development and Industrial Pharmacy (USA) V8 (3), pp. 283–396, 1982 "Some Properties of an Ethoxylated Caster Oil and Ethoxylated Oleyl Alcohol", Abstract 20/7/15.

L.C. Kingman, Cosmetics & Tioletries (USA), V95, (Apr.) pp. 23–26, 1980, "Pearl Pigments In Lotions and Creams", Abstract 20/7/16.

Meriaux–Brochu, et al., Can. J. Pharm. Sci., V12 (4), pp. 97–98, 1977, "Interaction Between Chlorpromazine Base and Oleyl Alcohol", Abstract 20/7/18.

H.O. Lin et al., Journal of Pharmaceutical Sciences (USA), V63 (Jan.) pp. 145–146, 1974, "Physical Properties of Four Polymorphic forms of sulfanilimide. 1. Densities, Refractive Indexes, and X–Ray Diffraction Measurements", Abstract 20/7/19.

N. H. Choulis, Can. J. Pharm. Sci., V6 (4), pp. 93–94, 1971 "Critical Micelle Concentration Determination of some Nonionic Surfactants", Abstract 20/7/21.

G. Viggiano et al., Bollettino Chimico Farmaceutico (Italy) V112, (Nov.) pp. 746–752, 1973, "Water–DMOS and Water– DMSO–Urea Systems", Abstract 20/7/20.
Derwent Abstract, JP05229936, Answer 1 of 14 Feb. 1992.
Derwent Abstract, EP–524579, Answer 2 of 14 May 1992.
Derwent Abstract, CS9102272, Answer 3 of 14 Jul. 1971.
Derwent Abstract, CS277548, "Manufacture of Hydrotalcite", Answer 4 of 14 Feb. 1993.
Derwent Abstract, CA1234761, "Chewable Aspirin Tablets—cont. Fatty Material and Buffer", Answer 5 of 14 Aug. 1984.
Derwent Abstract, EP–122463, "Soft Gelatin Antacid Capsules", Answer 6 of 14 Mar. 1983.
Derwent Absttact, EP90946, "Antacid di hydroxy aluminum sodium . . . carbon dioxide", Answer 7 or 14 Apr. 1982.
Derwent Abstract, PL–109002, "Dihydroxyaluminum Sodium Carbonate", Answer 8 of 14 May 1981.
Derwent Abstract, NL7806135, "Aluminum Hydroxide Gels", Answer 9 of 14 Dec. 1979.
Derwent Abstract, U.S. 4,115,553—"Chewable Antacid", Answer 10 of 14 Jun. 1974.
Derwent Abstract, BE–867982, "Sodium free aluminum hydroxide . . . earth carbonate", Answer 11 of 14 Jun. 1978.
Derwent Abstract, DE1467767, "Granules and Pills containing Stable . . . Neutralization Rate", Answer 12 of 14 Feb. 1970.
Derwent Abstract, DE1467767, "Polyethylene Glycol in Antacid Granules Tablets", Answer 13 of 14 Dec. 1965.
Derwent Abstract, DE1467767—"Antacid Granulates and Tablets", Answer 14 of 14 Dec. 1965.

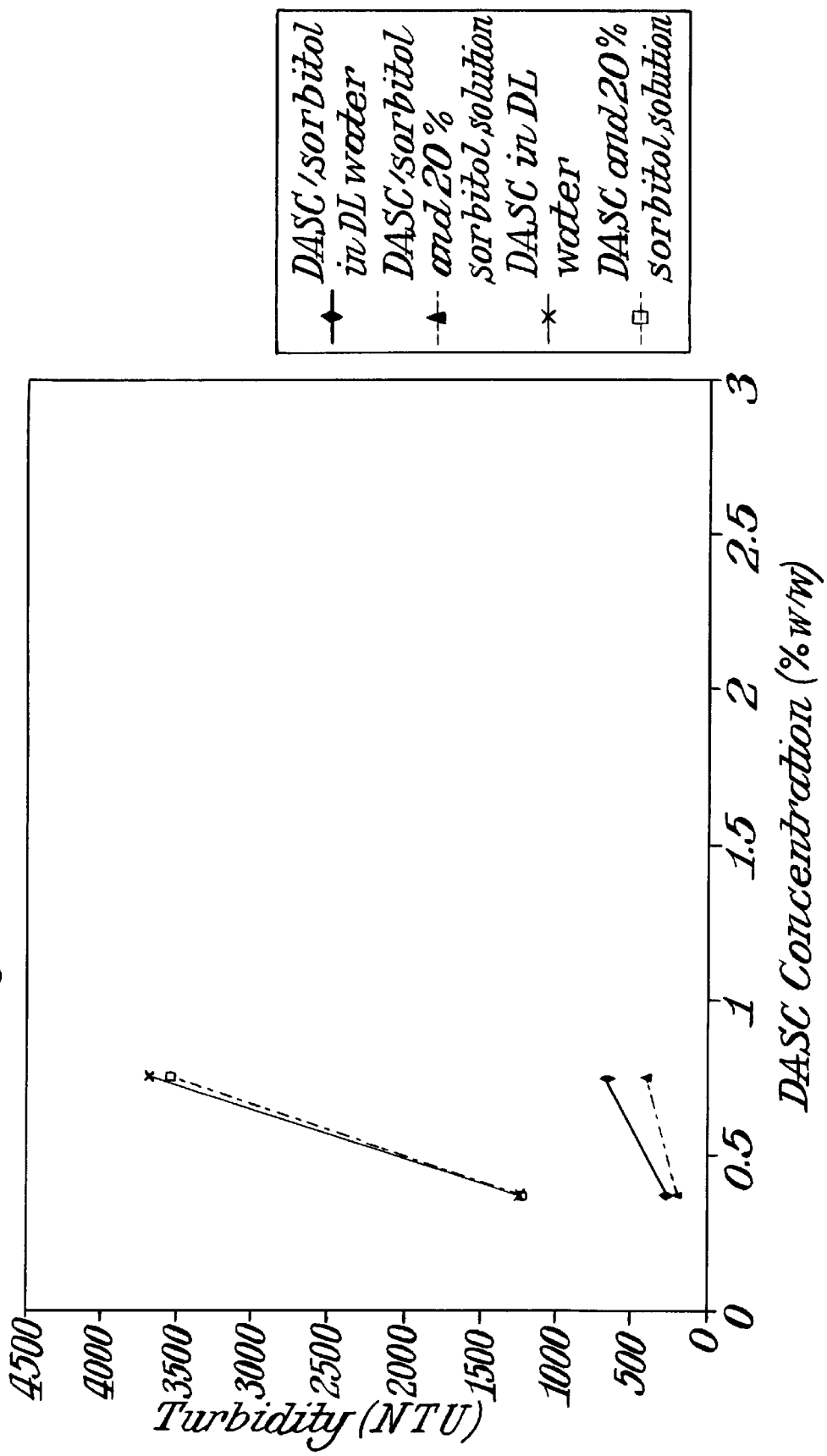

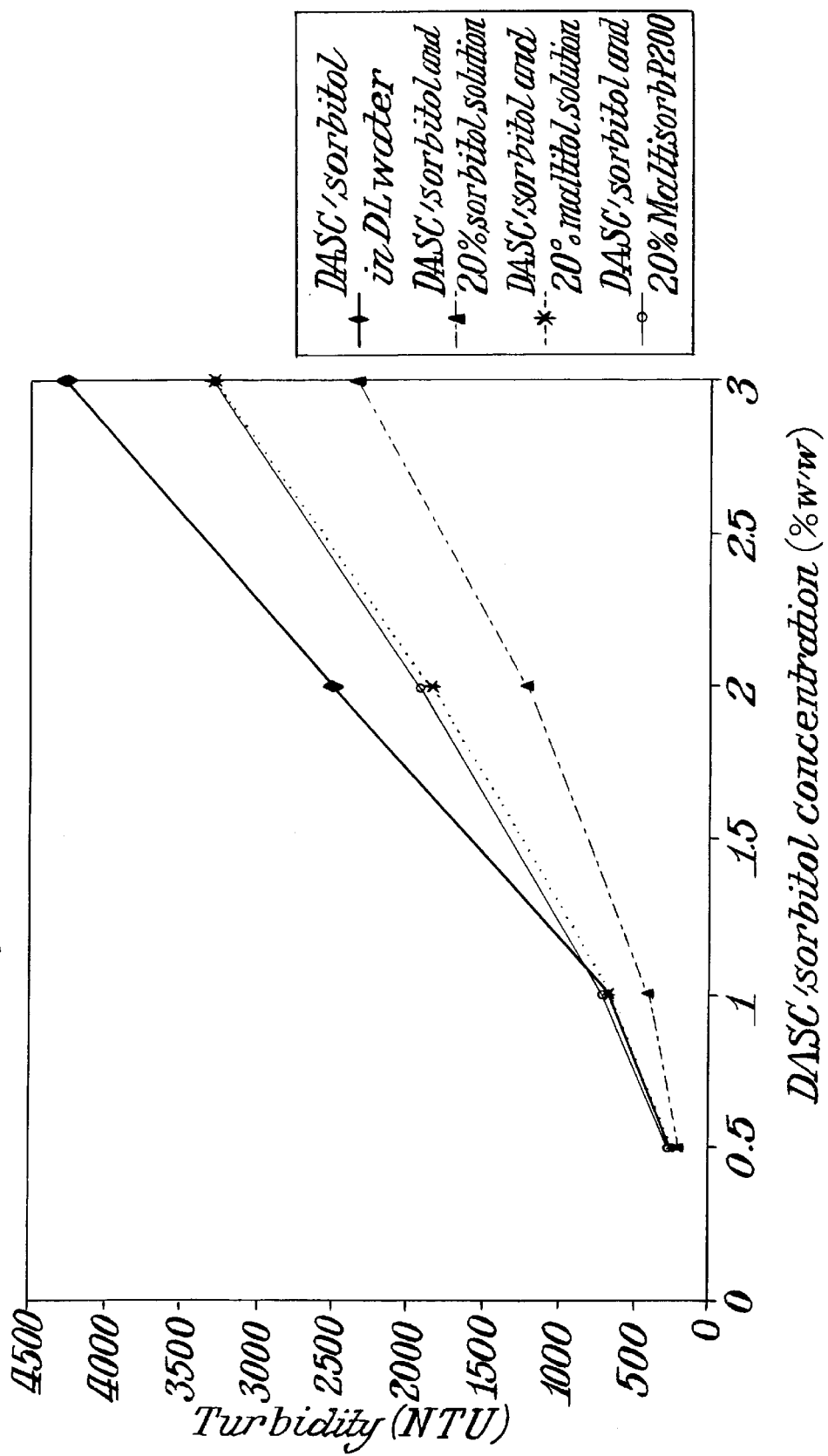

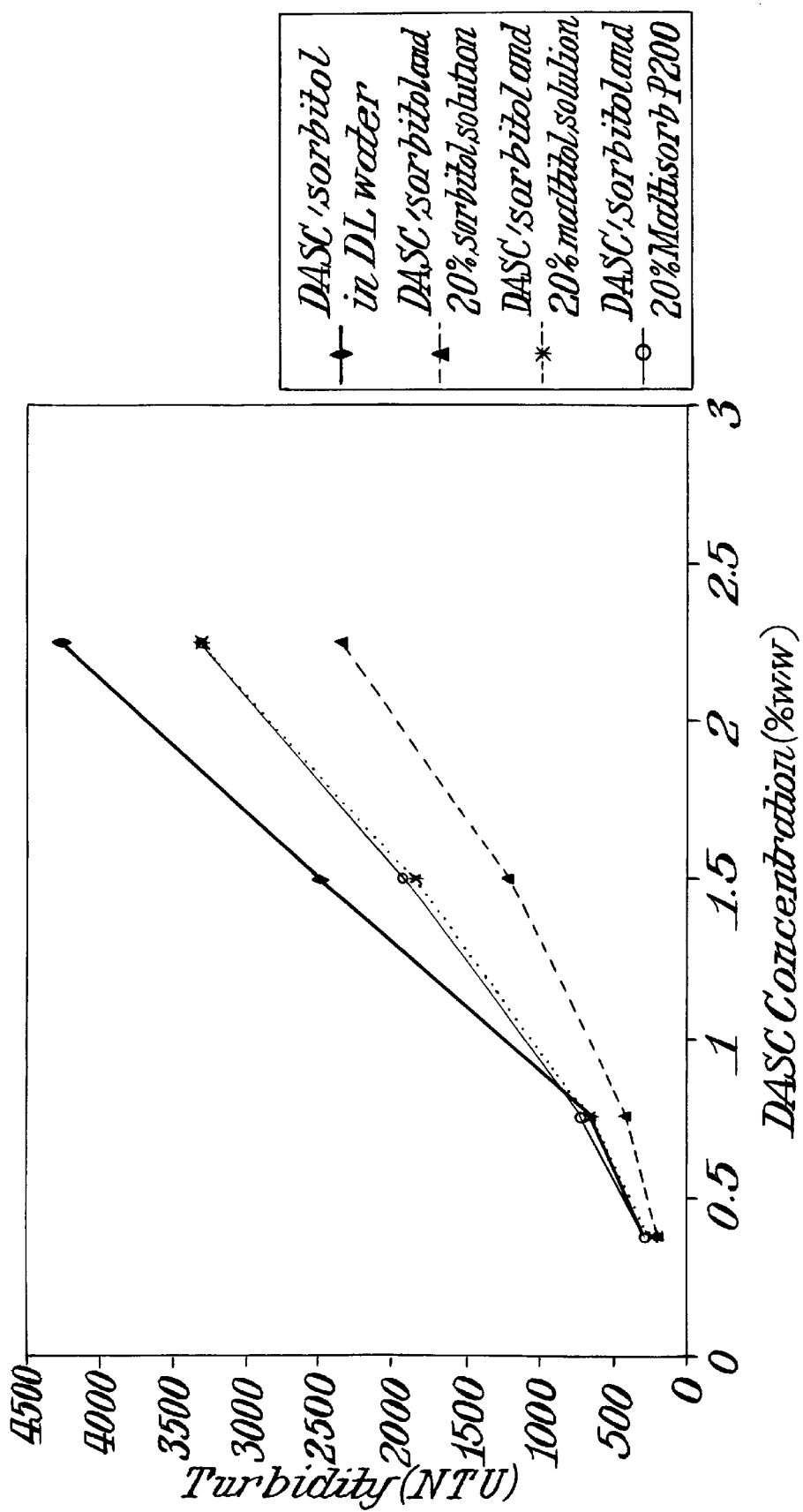

TRANSLUCENT ANTACID SUSPENSION CONTAINING CO-DRIED DIHYDROXY ALUMINUM SODIUM CARBONATE

FIELD OF THE INVENTION

The invention pertains to essentially translucent antacid compositions which contain dihydroxyaluminum sodium carbonate (DASC) co-dried with a polyol, and which may contain additional polyol to further enhance the translucency.

BACKGROUND AND PRIOR ART

Antacid suspensions are standard medications for the treatment of heartburn and other gastrointestinal disorders. Antacids neutralize the gastric acids created in the stomach. It is desirable that an antacid feature a high acid neutralization capacity and a rapid rate of gastric acid neutralization.

Antacids are available in the form of liquid suspensions or solid dosage forms. Liquid dosage forms are usually preferred over solid (tablets) because of their rapid action. Liquid antacid compositions are useful in the treatment of acute and chronic upper gastrointestinal disorders. The liquid antacids are usually indicated for the symptomatic relief of upset stomach associated with the hyperacidity also know as heartburn, acid indigestion and sour stomach.

A disadvantage associated with antacids in general (both liquid and solid forms) is an undesirable chalky taste. This can cause problems with patient compliance since patients tend not to use medications which are palatable. This is a disadvantage associated with antacids which are taken frequently for chronic treatment.

It is known in the art that conventional milling or homogenizing of antacid suspensions can alleviate the chalkiness to some degree but not entirely. For example, U.S. Pat. No. 4,533,543 (Morris et al.) describes improving the texture of solid antacid formulations by maintaining a small particle size, e.g. less than 500 millimicrons, and coating the particles with a mixture comprised of a fatty material or oil. U.S. Pat. No. 3,843,778 (Diamond) also discloses coating solid antacid particles, ranging in size from 0.05 to 300 microns, with an oil to create an improved texture.

Further, it is known in the art to use linear polyols, such as mannitol and sorbitol, specifically with aluminum hydroxide gels, to inhibit the polymerization reaction that occurs on aging. Shah et al., 70 J. Pharm. Sci. 1101–1104 (October 1981) teaches that polyols have a negative effect by reducing the rate of acid neutralization. Shah discloses that by carefully selecting the specific polyol and concentration, gel stabilization can be optimized.

Dihydroxyaluminum sodium carbonate (DASC) is a widely used gastric antacid. It has the formula $(HO)_2AlOCO_2Na$ and is typically prepared by a batch process in which aluminum isopropylate (i.e. aluminum isopropoxide) is contacted with an aqueous solution of sodium bicarbonate, see e.g. U.S. Pat. No. 2,783,179. Other methods of manufacture are known, see e.g. U.S. Pat. No. 4,438,085.

There is a need in the art to provide a liquid antacid composition containing DASC that is non-chalky and translucent in appearance. Translucency appeals to the patient/user because it connotes purity and good mouth feel, as opposed to the chalky, granular taste normally associated with liquid antacids.

SUMMARY OF THE INVENTION

The invention comprises an essentially translucent liquid antacid composition comprising dihydroxyaluminum sodium carbonate (DASC) co-dried with a polyol, preferably sorbitol. In the antacid composition, the co-dried DASC/polyol preferably comprises about 0.5 to about 5.0% by weight based on the total weight of the composition. The antacid composition also preferably contains an additional polyol to further enhance the translucency. The antacid composition may include formulation aids such as suspending agents, antigelling additives, surface modifiers, or preservatives.

BRIEF DESCRIPTION OF THE DRAWINGS

FIG. 1 is a graph of turbidity (NTU) v. DASC concentration for compositions containing co-dried DASC/sorbitol or conventional DASC.

FIG. 2 is a graph of turbidity (NTU) v. co-dried DASC/sorbitol concentration.

FIG. 3 is a graph of turbidity (NTU) v. DASC concentration.

DESCRIPTION OF THE PREFERRED EMBODIMENTS

It has been found that use of co-dried DASC/polyol forms a more translucent liquid antacid composition as compared to liquid compositions containing conventional DASC. The co-dried DASC/polyol is produced by, first, preparing DASC using conventional methods, such as by precipitation of aluminum isopropoxide with an aqueous solution of sodium bicarbonate. The precipitated DASC is filtered and washed under vacuum and the resulting wet cake is resuspended in water and polyol, e.g. sorbitol or maltitol. The resulting slurry is then spray-dried to produce a co-dried material which is pharmaceutically equivalent in antacid activity to commercially available DASC (see the Examples below).

The co-dried DASC/polyol normally contains approximately 50–90% DASC and 10–40% polyol/sorbitol by weight. To prepare the co-dried DASC/sorbitol, commercially available DASC and polyols may be used. It is preferred that the average particle size of the DASC used to make the co-dried material is less than about 1 micron, and more preferably less than about 0.5 microns.

To form the composition of the invention, the co-dried DASC/polyol is mixed with water or water and polyol to form an essentially translucent liquid antacid composition. Preferably, the co-dried DASC/polyol comprises approximately 0.5% to 5.0% by weight of the antacid composition. More preferably, the co-dried DASC/polyol comprises about 2.0 to about 5.0% by weight of the antacid composition. Most preferably, the co-dried DASC/polyol comprises about 3.0% to about 4.0% by weight of the antacid composition.

The term polyol refers to a non-toxic, pharmaceutically acceptable polyhydric alcohol. Suitable polyols include hydrogenated monosaccharides such as sorbitol, mannitol and xylitol, and hydrogenated disaccharides such as malitol, isomalt and lactitol. Sorbitol and mannitol are preferred polyols, with sorbitol being the most preferred.

Other possible components of the antacid suspension are conventional formulation aids such as suspending agents, antigelling additives, surface modifiers, preservatives, sweeteners, flavorants, waxes, colorants and diluents. Suitable additives include hydroxyethyl cellulose, hydroxypropyl methyl cellulose, sugars, sugar alcohols, saccharin, salts, parabens, such as butyl and methyl parabens, and ethylenediamine tetra-acetic acid. It is anticipated that the antacid of the present invention may be combined with effective amounts of other active ingredients, such as antifoaming agents like simethicone, histamine $H_2$-receptor-antagonists like cimetidine, ranitidine, nizatidine and famotidine, and proton-pump inhibitors such as omeprazole and lansoprazole.

A suspension formed from co-dried DASC and water is preferably combined with additional polyol to further enhance the translucency. The additional polyol as added may be in the form of a solid powder or an aqueous solution concentrated to 50–80% polyol by weight. For example, USP sorbitol solution, which is 70% w/w polyol, may be used. Preferably, about 10% to about 30% polyol solution (e.g. USP) is used to enhance translucency. Most preferably, about 20% additional polyol is used.

With or without the additional polyol, the resulting antacid composition is essentially translucent. By essentially translucent is meant translucent to the naked eye. In optical measurements, the composition would typically measure less than about 2000 NTU, preferably less than about 1500 NTU, and most preferably less than about 1000 NTU.

The concentration of the effective ingredient can vary depending on desired antacid strength. The invention allows for translucency of the liquid composition while maintaining a high ANC (Acid Neutralizing Capacity) value. Translucency has been maintained for ANC values as high as about 10.5 mEq/15 ml or higher.

The composition of the invention provides fast-acting antacid relief and high acid neutralizing capacity, with good mouth feel characteristics and desirable appearance. The antacid suspension retains substantial efficacy over a standard shelf life. Furthermore, the antacid formulation is slow settling and exhibits thixotropic properties.

A preferred formulation is as follows (all percentages are expressed as weight based on the total weight of the finished formulation). The antacid composition contains co-dried 75% DASC/25% sorbitol (by weight) in an amount effective for pharmaceutical purposes, typically about 0.5 to 5.0% by weight, approximately 67.0% to about 81.0%% by weight of water, and 10–30% by weight additional polyol. The composition may contain about 0.05% to about 0.5% by weight suspending agents, preferably hydroxyethyl cellulose, and about 0.02% to about 0.07% by weight antigelling agents, preferably edetate disodium.

One advantage of the invention herein is that preservatives are not needed in the final formulation due to the basic nature of DASC. However, preservatives may be added, in effective amounts of about 0.01% to about 0.05% by weight. The composition may also contain about 0.01% to about 0.05% by weight sweeteners, e.g. sodium saccharin. The composition will preferably contain approximately 0.2% to about 1.2% by weight flavorants and approximately 0.04% to about 0.4%% by weight food dyes.

A currently most preferred formulation is as follows: about 75.5% purified water, about 20.0% sorbitol solution (USP), about 0.12% hydroxyethyl cellulose; about 3.4% codried DASC/sorbitol, about 0.047% edetate disodium, about 0.30% sodium carbonate, about 0.0275% sodium saccharin, about 0.58% flavorants (e.g. 0.35% peppermint and 0.22% alpine creme) and about 0.00095% dyes (e.g. 0.00065% blue #1 dye and 0.00030% yellow #10 dye).

By way of explanation, it is understood that those skilled in the art need only understand the nature of the recipe for the starting materials to make the antacid composition of the invention herein. It is well understood in this particular art that one can describe the final product by referring back to the precursor or starting materials, since such a description is sufficient for the reproducibility of the product.

The composition of the invention my be prepared as follows. First, the additional polyol is dissolved in water. Optionally, a suspending agent, such as hydroxyethyl cellulose (HEC), may be added to the polyol/water mixture and mixed until the polyol and suspending agent are completely dissolved. The co-dried DASC/polyol (i.e. DASC/sorbitol) is added to the solution and thoroughly mixed until the liquid is free of lumps. Once the codried DASC/sorbitol has been dispersed in the polyol solution, other optional formulation aids may be added. The suspension is then milled and pasteurized.

The invention is further illustrated by the following examples.

EXAMPLES

Example 1

A formulation of essentially translucent liquid antacid containing co-dried DASC/sorbitol as the effective ingredient was prepared by the following steps. For reference, Table I lists the ingredients in percent by weight and weight in grams of the ingredients used in the example.

250 g of purified water (Part A) is added to a two liter vessel equipped with a mixer. To the vessel, 470 mg of edetate disodium is added and mixed until dissolved. 200 g of a sorbitol solution (USP) is added with mixing. 1.2 g of hydroxyethyl cellulose is added with mixing until the polymer is hydrated. Next, 34 g of co-dried dihydroxyaluminum sodium carbonate/sorbitol is added with mixing until the liquid material is free of lumps.

A further 505.25 g of purified water (Part B) is added, as are 3 g of sodium carbonate and 275 mg of sodium saccharin. The following are added with mixing: 3.5 g peppermint flavor, 2.2 g alpine creme flavor, 7 mg of blue #1 dye, and 3 mg of yellow #10. The final mixture is passed through a mill and pasteurizer.

TABLE I

| Ingredients | Weight % | Weight (g) |
| --- | --- | --- |
| Purified Water (Part A) | 25.00000 | 250.000 |
| Sorbitol Solution | 20.00000 | 200.000 |
| Hydroxyethyl Cellulose | 0.12000 | 1.200 |
| DASC/sorbitol (co-dried) | 3.40000 | 34.000 |
| Edetate Disodium | 0.04700 | 0.470 |
| Purified Water (Part B) | 50.52455 | 505.250 |
| Sodium Carbonate | 0.30000 | 3.000 |
| Sodium Saccharin | 0.02750 | 0.275 |
| Peppermint Flavor | 0.36000 | 3.600 |
| Alpine Creme Flavor | 0.22000 | 2.200 |
| Blue #1 Dye | 0.00065 | 0.007 |
| Yellow #10 Dye | 0.00030 | 0.003 |
| TOTAL | 100.00000 | 1000.000 |

Examples 2–8 and Comparative Examples A–F

Examples of varying composition were prepared essentially as described above to compare translucency and acid neutralizing capacity (ANC) of samples containing conventional DASC and samples prepared with co-dried DASC/sorbitol as the active ingredients, and to determine how the presence of additional polyol(s) affected translucency. The translucency and ANC of deionized water and the commercial antacid Mylanta® were also tested for comparison purposes.

The level of translucency was measured in NTU values (nephelometric turbidimetric units) of turbidity. The turbidity measurements were made using a turbidimeter (HACH model 2100N). As controls, water was considered to be clear and dilution of the commercial liquid antacid was considered unacceptably opaque. As Table II shows, the turbidity of water is less than 1 NTU, whereas the turbidity the commercial antacid liquid is greater than 3000 NTU.

As can be seen from Table II, at equivalent acid-neutralizing capacity values, the co-dried DASC/sorbitol compositions demonstrated significantly lower NTU values than DASC compositions. At equivalent levels of DASC/sorbitol, the turbidity of the liquid composition is further reduced by the addition of a 20% by weight solution of sorbitol or malitol as additional polyol. Importantly, the addition of sorbitol or malitol did not significantly affect the acid neutralizing capacity. Additives such as HEC or propylene glycol only slightly increase the turbidity values of DASC/sorbitol preparations.

TABLE II

| Example | Formula | Weight % | Turbidity NTU'S | ANC (mEq/1 5 ml) |
|---|---|---|---|---|
| A | Deionized (DI) Water | 100 | 0.128 | 0 |
| B | Mylanta, regular strength, diluted | 0.024 | 3041 | 0.92 |
| C | DASC in DI water | 0.375 | 1252 | 1.46 |
|   |   | 0.750 | 3688 | 2.93 |
|   |   | 1.500 | >4500 | 5.88 |
|   |   | 2.250 | >4500 | 8.86 |
| 2 | DASC/sorbitol in DI water | 0.5 | 274 | 1.47 |
|   |   | 1.0 | 675 | 2.93 |
|   |   | 2.0 | 2511 | 5.89 |
|   |   | 3.0 | 4270 | 8.88 |
|   |   | 5.0 | >4500 | 14.98 |
| D | DASC and 20% sorbitol in DI water | 0.375 | 1227 | 1.54 |
|   |   | 0.750 | 3545 | 3.09 |
|   |   | 1.500 | >4500 | 6.20 |
| 3 | DASC/sorbitol and 20% sorbitol solution in DI water | 0.5 | 205 | 1.54 |
|   |   | 1.0 | 415 | 3.09 |
|   |   | 2.0 | 1213 | 6.20 |
|   |   | 3.0 | 2340 | 9.35 |
|   |   | 5.0 | >4500 | 15.80 |
| E | DASC and 20% malitol solution in DI water | 0.375 | 1040 | 1.55 |
|   |   | 0.750 | 3207 | 3.10 |
|   |   | 1.500 | >4500 | 6.22 |
| 4 | DASC/sorbitol and 20% malitol solution in DI water | 0.5 | 249 | 1.55 |
|   |   | 1.0 | 664 | 3.11 |
|   |   | 2.0 | 1849 | 6.25 |
|   |   | 3.0 | 3295 | 9.42 |
|   |   | 5.0 | >4500 | 15.90 |
| F | DASC and 20% maltisorb P200 in DI water | 0.375 | 1091 | 1.58 |
|   |   | 0.750 | 3077 | 3.16 |
|   |   | 1.500 | >4500 | 6.35 |
| 5 | DASC/sorbitol and 20% Maltisorb P200 in DI water | 0.5 | 275 | 1.58 |
|   |   | 1.0 | 723 | 3.17 |
|   |   | 2.0 | 1917 | 6.38 |
|   |   | 3.0 | 3284 | 9.63 |
|   |   | 5.0 | >4500 | 16.19 |
| 6 | DASC/sorbitol and 0.12% HEC in DI water | 0.5 | 381 | 1.46 |
|   |   | 1.0 | 934 | 2.93 |
|   |   | 2.0 | 2946 | 5.90 |
|   |   | 3.0 | 4237 | 8.89 |
| 7 | DASC/sorbitol and 0.5% HEC in DI water | 0.5 | 463 | 1.46 |
|   |   | 1.0 | 1358 | 2.94 |
|   |   | 2.0 | 3506 | 5.90 |
|   |   | 3.0 | >4500 | 8.90 |
| 8 | DASC/sorbitol and 5% propylene glycol in DI water | 0.5 | 475 | 1.47 |
|   |   | 1.0 | 1364 | 2.94 |
|   |   | 2.0 | 3448 | 5.91 |

NTU = Nephelometric Turbidimetric Units measured using HACH Turbidimeter
ANC = Acid Neutralizing Capacity
Maltisorb P200 = malitol added in crystalline powder form Other embodiments of the invention will be apparent to those skilled in the art from consideration of the specification and practice of the invention disclosed herein.

What is claimed is:

1. An essentially translucent aqueous antacid composition comprising from about 0.5 to about 5.0% by weight of co-dried DASC/polyol as an antacid active ingredient and containing about 10 to about 30% by weight of an additional polyol to render the composition essentially translucent.

2. The antacid composition of claim 1 wherein the polyol in the co-dried DASC/polyol is sorbitol.

3. The antacid composition of claim 1, prepared by mixing 0.5 to 5% by weight of co-dried DASC polyol and 10–30% by weight additional polyol, in each case based on weight of composition, with water.

4. The antacid composition of claim 3, wherein the additional polyol is sorbitol.

5. The antacid composition of claim 1 wherein the co-dried DASC/polyol contains from about 50% to about 90% DASC and about 10% to about 40% polyol by weight, based on weight of the co-dried DASC/polyol.

6. The antacid composition of claim 1 wherein the additional polyol is one or more polyols selected from the group consisting of hydrogenated monosaccharides and hydrogenated disaccharides.

7. The antacid composition of claim 6 wherein the additional polyol is sorbitol, mannitol, malitol, xylitol, lactitol or isomalt.

8. The antacid composition of claim 7 wherein the additional polyol is sorbitol.

9. The antacid composition of claim 7 wherein the additional polyol is malitol.

10. The antacid composition of claim 1 wherein the composition has a turbidity of less than about 2000 NTU.

11. The antacid composition of claim 1 wherein the composition has a turbidity of less than about 1500 NTU.

12. The antacid composition of claim 1 wherein the composition has a turbidity of less than about 1000 NTU.

13. The antacid composition of claim 1 wherein the composition additionally contains suspending agents, anti-gelling additives, preservatives, sweeteners, flavorants, colorants or diluents.

* * * * *